(12) United States Patent
Tsen et al.

(10) Patent No.: US 7,259,256 B2
(45) Date of Patent: Aug. 21, 2007

(54) PRIMERS USEFUL IN POLYMERASE CHAIN REACTION FOR THE IDENTIFICATION OF SUBTYPES C1, C2 AND C3 OF STAPHYLOCOCCAL ENTEROTOXIN TYPE C

(75) Inventors: Hau-Yang Tsen, Taichung (TW); Tong-Rong Chen, Chiai (TW)

(73) Assignee: National ChungHsing University, Taichung (TW)

(\*) Notice: Subject to any disclaimer, the term of this patent is extended or adjusted under 35 U.S.C. 154(b) by 1022 days.

(21) Appl. No.: 10/261,467

(22) Filed: Oct. 2, 2002

(65) Prior Publication Data

US 2006/0257864 A1  Nov. 16, 2006

(51) Int. Cl.
*C07H 21/02* (2006.01)
*C07H 21/04* (2006.01)
*C12Q 1/68* (2006.01)
*C12P 19/34* (2006.01)

(52) U.S. Cl. ............... 536/24.3; 536/23.1; 536/24.32; 435/6; 435/91.2

(58) Field of Classification Search ................ None
See application file for complete search history.

*Primary Examiner*—Teresa E. Strzelecka
(74) *Attorney, Agent, or Firm*—Rosenberg, Klein & Lee

(57) ABSTRACT

The invention provides primers designed on base of the difference of sequences among staphylococcal enterotoxin subtypes, i.e., $C_1$, $C_2$ and $C_3$. The invention also provides a PCR method for detecting subtypes of staphylococcal enterotoxin type C by using the above-mentioned primers. The invention relates also to DNA probes useful for the identification of subtypes $C_1$, $C_2$ and $C_3$ of staphylococcal enterotoxin type C in various food and clinical samples. The primers of the invention comprises following sequences:

ENTC1 5'-ACAGA GTTAT TAAAT GAAGG-3';
ENTC2 5'-GTATC AGCAA CTAAA GTTAT-3';
ENTC3 5'-AAGAG ATTAT TTATT TCACGT-3';
ENTCR 5'-ATCAT ACCAA AAAGT ATTGC-3'.

2 Claims, 2 Drawing Sheets

US 7,259,256 B2

PRIMERS USEFUL IN POLYMERASE CHAIN REACTION FOR THE IDENTIFICATION OF SUBTYPES C1, C2 AND C3 OF STAPHYLOCOCCAL ENTEROTOXIN TYPE C

BACKGROUND OF THE INVENTION

1. Field of the Invention

The invention relates to primers designed on base of the difference of sequences among staphylococcal enterotoxin subtypes, and to a PCR method for detecting subtypes (i.e., $C_1$, $C_2$ and $C_3$) of staphylococcal enterotoxin type C by using the above-mentioned primers. The invention relates also to DNA probes useful for the identification of subtypes $C_1$, $C_2$ and $C_3$ of staphylococcal enterotoxin type C in various food and clinical samples.

2. Description of the Prior Art

Staphylococcal aureus is one of the important pathogens for food poisoning. Staphylococcal aureus can produces a variety of staphylococcal enterotoxin, i.e. staphylococcal enterotoxin A-B-C-D-E and also, to a lesser extent, G-H-I and J (Genigeorgis, 1989; Betley and Harris, 1994; Su and Wong, 1995; Munson et al., 1998; Zhang. et al., 1998).

Staphylococcal enterotoxin C comprises a group of highly conserved proteins, and exhibits a considerable immunological crossover reaction (Marr. et al., 1993). Protein sequence of staphylococcal enterotoxin C present predominantly subtypes of SEC1, C2 and C3 and other minor subtypes (Bohach and Schlievert, 1987; Couch and Betley, 1989; Hovde. et al., 1990; Marr et al., 1993). Since homologies of the amino acid sequences among subtypes C1, C2 and C3 of staphylococcal enterotoxin C are greater than 98% (Bohach and Schlevert, 1987; Hovde. Et al., 1990; Betley. et al., 1992), the identification thereof is not easy.

At present, methods for detecting staphylococcal enterotoxin types include, for example, commercially available immuno-detecting kit based on the serological characteristics of staphylococcal enterotoxin, such as, staphylococcal enterotoxin reverse phase latex agglutination (SET-RPLA) kit (Denka. Seiken, Tokyo, Japan); and kits developed based on enterotoxin themselves, such as staphylococcal enterotoxin ELISA (SET-EIA) (Sarasota, Fla., USA) or TECRA (Bioenterprises Pty. Ltd, Roseville, Australia). These kits detect mainly staphylococcal enterotoxin A, B, C, D and E. No publication in literatures reported any DNA assay for the identification of staphylococcal enterotoxin subtypes C1, C2 and C3. As detecting method by means of a gene, though there was a study for detecting staphylococcal enterotoxin types A, B, C, D and E by polymerase chain reaction (PCR) with a specific DNA probe (Johnson. et al., 1991; Tsen and Chen, 1992; Tsen et al., 1994; Schmitz. et al., 1998), no DNA probe or PCR method is available for subtyping staphylococcal enterotoxin C1, C2 and C3, except of the PCR primers for the identification of staphylococcal enterotoxin subtypes $C_1$, $C_2$ and $C_3$ developed by the invention. Moreover, in case of food poisoning and large-scale food poisoning caused by staphylococcal enterotoxin type C, no method is available for identify further the subtype of the staphylococcal enterotoxin type C.

There are a few relating patents such as, for example, ROC patent No. 80100762 titled "Rapid identification of Staphylococcal aureus by the agglutination of micro-latex particles"; ROC patent No. 82106016 titled "Rapid identification of Staphylococcal aureus in processed food by enzymatic immunological analytical method"; EP 1160333A2, "Oligonucleotides and method for detection of mecA gene of methicillin-resistant *Staphylococcus aureus*"; U.S. Pat. No. 6,022,682, "Article and method for detection of enterotoxigenic staphylococci (1996)"; U.S. Pat. No. 563,536 (1995) 7, "Method for detecting staphylococci"; U.S. Pat. No. 5,582,974, "Nucleic acid probes for the detection of *Staphylococcus aureus* (1993)"; U.S. Pat. No. 5,443,963, "Method for detecting staphylococci (1994)"; U.S. Pat. No. 5,132,210 (1989), "Diagnostic test for Staphylococcal mastitis"; U.S. Pat. No. 4,849,341 (1986), "Diagnostic test for Staphylococcal mastitis in cattle"; U.S. Pat. No. 5,770,375 (1997), "Probe for diagnosing *Staphylococcus epidermidis*"; U.S. Pat. No. 5,776,712 (1998), "Methods and materials for the detection of *Staphylococcus aureus*"; U.S. Pat. No. 5,496,706 (1996), "Methods and materials for the detection of *Staphylococcus aureus*"; U.S. Pat. No. 5,437,978 (1993), "Detection for *Staphylococcus* spp."; and U.S. Pat. No. 5,702,895 (1996), "Method and kit for detecting methicillin-resistant *Staphylococcus aureus*".

SUMMARY OF THE INVENTION

Accordingly, the main object of the invention is to provide primers useful in the polymerase chain reaction for the identification of subtypes $C_1$, $C_2$ and $C_3$ in staphylococcal enterotoxin type C, which primers are designed based on parts of gene sequences with greater difference among of staphylococcal enterotoxin subtypes $C_1$, $C_2$ and $C_3$, and which are assigned into three pairs of PCR primers with following specificities:

SEQUENCE ID NO. 1: ACAGA GTTAT TAAAT GAAGG

ATCAT ACCAA AAAGT ATTGC

SEQUENCE ID NO. 2: GTATC AGCAA CTAAA GTTAT

ATCAT ACCAA AAAGT ATTGC

SEQUENCE ID NO. 3: AAGAG ATTAT TTATT TCACGT

ATCAT ACCAA AAAGT ATTGC

Another object of the invention is to provide a method for the identification of subtypes of staphylococcal enterotoxin C, in order to identify further the subtype of the staphylococcal enterotoxin type C in case of food poisoning and large-scale food poisoning caused by staphylococcal enterotoxin type C.

Yet another object of the invention is to provide DNA probes useful in PCR reaction for the identification of subtypes $C_1$, $C_2$ and $C_3$ in staphylococcal enterotoxin type C, which probes comprise of the above primers SEQ. ID NO. 1-SEQ. ID NO. 3 based on the specificities of above-mentioned primers with respect to staphylococcal enterotoxin subtypes $C_1$, $C_2$ and $C_3$ gene.

BRIEF DESCRIPTION OF THE DRAWINGS

The invention, as well as its many advantages, may be further understood by the following detailed description and drawings in which:

FIG. 1 shows the PCR detection of SEC *S. aureus* and bacterial strains other than SEC *S. aureus* using experimental conditions as described in Materials and Methods. (A) Lane a, 100-bp ladder; Lanes b through q represent PCR products amplified from SEC 1 *S. aureus* (FRI 137), SEC *S. aureus* (CCRC12654), SEA *S. aureus* (CCRC 12657), SEB *S. aureus* (CCRC 12653), SEC2 *S. aureus* (FRI 361), SEC3 *S. aureus* (FRI 913), SED *S. aureus* (CCRC 12660), SEE *S. aureus* (CCRC 12656), SETSST-1 *S. aureus* (CCRC 13831), SEG *S. aureus* (FRI 572), SHE *S. aureus* (FRI 569), SEI *S.* aureus (FRI 445), *S. aureus* (CCRC 011), *S. epidermids* (CCRC 11030), *Streptococcus mutans* (CCRC 10793), *Bacillus cereus* (CCRC 10603), *Clostridium perfringens* (CCRC 10914). (B) Lane a, 100-bp ladder; Lanes b through q represent PCR products amplified from SEC2 *S. aureus* (FRI 361), SEA *S. aureus* (CCRC 12657), SEB *S. arueus* (12653), SEC1 *S. aureus* (FRI 137), SEC3 *S. aureus* (FRI 913), SED *S. aureus* (CCRC 12660), SEE *S. aureus* (CCRC 12656), SETSST-1 *S. aureus* (CCRC 13831), SEG *S. aureus* (FRI 572), SHE *S. aureus* (FRI 569), SEI *S. aureus* (FRI 445), *S. aureus* (CCRC 011), *S. epidermids* (CCRC 11030), *Streptococcus mutans* (CCRC 10793), *Bacillus cereus* (CCRC 10603), *Clostridium perfringens* (CCRC 10914). (C) Lane a, 100-bp ladder; Lanes b through q represent PCR products amplified from SEC2 *S. aureus* (FRI 361), SEA *S. aureus* (CCRC 12657), SEB *S. aureus* (12653), SEC1 *S. aureus* (FRI 137), SEC3 *S. aureus* (FRI 913), SED *S. aureus* (CCRC 12660), SEE *S. aureus* (CCRC 12656), SETSST-1 *S. aureus* (CCRC 13831), SEG *S. aureus* (FRI 572), SHE *S. aureus* (FRI 569), SEI *S. aureus* (FRI 445), *S. aureus* (CCRC 011), *S. epidermids* (CCRC 11030), *Streptococcus mutans* (CCRC 10793), *Bacillus cereus* (CCRC 10603), *Clostridium perfringens* (CCRC 10914).

Figure 1:
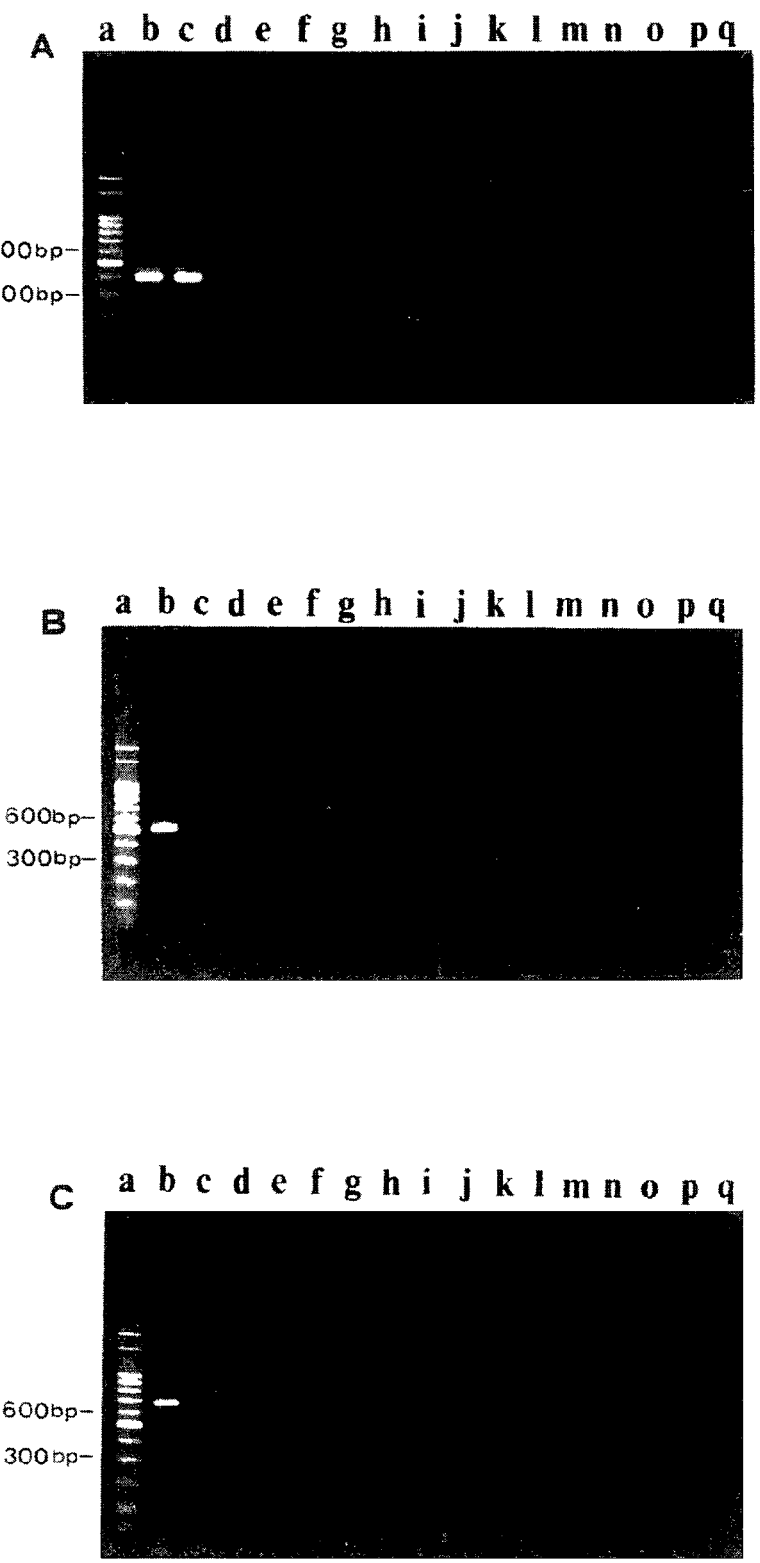

In FIG. 1, lanes that do not show bands are empty as the PCR product was not produced by the non-staphylococcal strains represented by those lanes. Such shows the specificity for the identification of subtypes $C_1$, $C_2$ and $C_3$ of staphylococcal enterotoxin type C.

Figure 2:
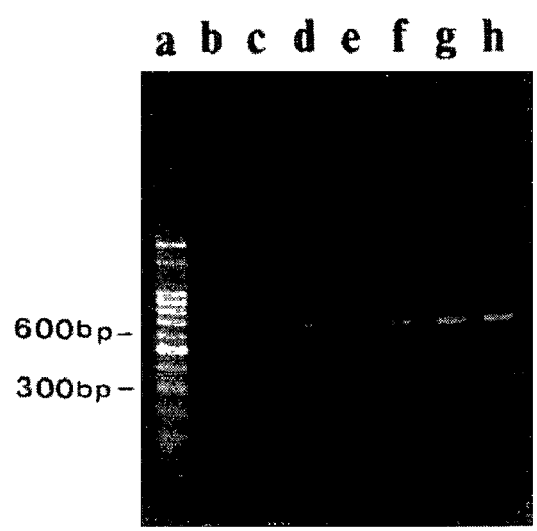

FIG. 2 shows the sensitivity for PCR detection of SEC3 *S. aureus* strain (FRI 913) using ENTC3/ENTCR primers. Experimental conditions were as described in Materials and Methods. Lane a, 100-bp ladder; Lanes b through h represent PCR products amplified from $N \times 10^0$ to $10^6$ CFU per assay of *S. aureus* cells. N equals to 1~9.

DETAILED DESCRIPTION OF THE PREFERRED EMBODIMENTS

The invention will be now described below with reference to the drawings.

Reagents and Materials:

A. Bacterial Strains:

Standard strains used in the method according to the invention and sources thereof listed in Table 1 are consisted of 10 *S. aureus* strains producing enterotoxin of types A, B, C1, C2, C3, D, E, G, H, I and 1 strain producing toxic shock syndrome toxin-1 (TSST-1). Table 2 lists other non-*S. aureus*, including *Bacillus cereus, Bacillus coagulars, Micrococcus varians, Staphylococcus epidermidis, Streptococcus mutans, Escherichia coli*. Table 3 lists 39 *S. aureus* strains producing enterotoxin C, which were provided by the Third Branch of Disease Control Agency, Department of Health, Taiwan, ROC (previously the Middle Examination Station of the Preventive Medical Institute) and were isolated from samples collected in food poisoning cases during 1995 to 2000. Table 4 lists 10 *S. aureus* strains producing enterotoxin of type C provided by the Food Research Center (FRI) of the University of Wisconsin, Madison, Wis., USA.

B. Media:

The medium used in the method according to the invention contains, as ingredients, Tryptic Soy Broth (TSB), Brain Heart Infusion (BHI), Baird-Parker agar base (BP), Mueller-Hinton agar, Plate Count Agar (PCA), and Egg Yolk Tullurite (EY) (all available from Detroit, Mich. USA).

C. Reagents:

Reagents used in the method according to the invention include Sodium dodecyl sulfate (SDS), Ethylenediamine tetra-acetic acid (EDTA), lysozyme, RNase and mineral oil (all available form Sigma Chemical Company, St. Louis, Mo., USA). Tris-(hydroxymethyl)-aminomethane, Triton X-100, proteinase K, dATP, dCTP, dGTP and dTTP (Boegeringer Mannhein GmbH Biochemica, Mannheim, Germany); Lysostaphin (Applied Microbiology, New York, USA); Agarose (Bio-Rad, Hercules, Calif., USA); N-Lauroylsarcosine Na-salt (Heidelberg, N.Y., USA); thermo-stable DNA Polymerase, ProZyme, (PROtech Technology Ent. Co., Ltd., USA); 100 bp ladder (Pharmacia, Uppsala, Sweden); chloroform (Alps, Taiwan), $MgCl_2$, NaCl, Sodium Citrate, NaOH, Boric Acid, KCl (Wako Pure Chemical Industry, Ltd., Osaka Japan). All reagents used in the method according to the invention are of reagent grade of molecular biology grade.

D. Immunological Analytical Kits:

Immunological analytical kits, SET-RPLA (Staphylococcal Enterotoxin A, B, C, D, detection kit by Reversed Passive Latex Agglutination) is available from Denka Seiken, Tokyo, Japan).

E. Buffer Solutions:

Buffer solutions used in the method according to the invention are as follow:

1. 50×TAE Buffer:
   242 g Tris-HCl, 57.1 ml glacial acetic acid 100 ml 0.5 M EDTA, pH8.0, and water to 1000 ml.

2. PIV Buffer:
   1 M NaCl, 10 mM EDTA, pH 7.6.

3. Chloroform-Isoamyl Alcohol Mixture:
   Chloroform and isoamyl alcohol mixed at volume ratio of 24:1.

4. Lysostaphin Buffer (EC Buffer)
   6 mM Tris-HCl (pH 7.6), 1 M NaCl, 100 mM EDTA, 0.5% Brij 58, 0.2% deoxycholate, and 0.5% sodium lauroyl sacosin.

5. 10×PCR Buffer
   100 mM Tris-HCl, pH 8.3; 500 mM KCl, 60 mM $MgCl_2$, 0.1% Gelatin, and 1% Triton X-100.

F. PCR Thermocycler:
   PCR thermocycler used in the PCR is the Perkin Elmer Gene Amp PCR system 9600 (Perkin-Elmer Coporation, Norwalk, Conn., USA).

G. Detection of Staphylococcal Enterotoxin
   Detection of staphylococcal enterotoxin is carried out by RPLA according to the instruction provided by Denka Seiken and comprises following steps:

1. Production of Staphylococcal Enterotoxin
   *S. aureus* on a TSA slant was inoculated in 5 ml BHI broth at 37° C., and incubated by shaking at 160 rpm for 18~24 hours.

2. Treatment of Samples
   One ml aliquot of the above bacterial suspension was centrifuged in a 1.5-ml micro-centrifuge tube at 3000 rpm for 20 minutes. The supernatant thus obtained was used for assay.

3. RPLA Assay
   To each well of a V-shaped 96-well plate, 25 μl each of sensitized latex A, B, C, or D was added, and, after shaking at 60 rpm for 10 minutes, was incubated at room temperature for 18-24 hours and then observed the result. Separately, standard enterotoxin A, B, C, and D was added into sensitized latex A, B, C, or D and used as positive control, while standard enterotoxin A, B, C, and D was added into non-sensitized control latex A, B, C, or D and used as negative control.

H. Extraction of Total DNA from *Staphylococcus aureus*

A platinum ear amount of bacteria was incubated in 3 ml TSB broth at 37° C. for 12 hours. A 0.5 ml aliquot of bacteria suspension was centrifuged in a micro-centrifuge at 5000 rpm for 7 minutes. The supernatant was discarded. After adding 250 μl of lysostaphin buffer and shaking homogeneously, 25 μl lysostaphin (2 mg/ml), 25 μl lysozyme (2 mg/ml), and 20 μl RNase (2 mg/ml) were added and the mixture was reacted at 37° C. for 2-3 hours to a clear solution. 25 μl proteinase K (10 mg/ml) was added and the mixture was reacted again at 65° C. for 3-4 hours to a clear solution. The reaction mixture was then extracted with an equal volume of saturated phenol-chloroform. After centrifuging at 13000 rpm for 10 minutes, the supernatant was transferred to a new micro-centrifuge and extracted again with an equal volume of saturated phenol-chloroform. The procedure was repeated once. Finally, it was extracted once with equal volume of chloroform. To the supernatant thus obtained was added two volume of 95% ethanol and the resulting mixture was allowed to precipitated at −70° C. for 1 hour. Thereafter, the mixture was centrifuged at 13000 rpm for 15 minutes. The supernatant was discarded. The pellet washed once with 70% ethanol, centrifuged, dried, an appropriate amount of sterile distilled water (30-40 μl) was added to dissolve it and then stored at 4° C. till used.

I. PCR Primers

Since there is a homology of greater than 97% among gene sequences of enterotoxin C1, C2 and C3, the part of sequence having difference among them is used to design primers useful in PCR. For this purpose, sequence data was obtained by searching through Gopher system Internet connected to biological molecular database Gene Bank/EMBL/DDBJ. The sequence data was subjected to multiple sequence format alignment by means of Wisconsin Sequence Analysis Software Package developed by Genetic Computer Group (GCG) to find out the difference among gene sequences, thereby, based on the difference thus obtained, 4 PCR primers having detection specificity to genes of enterotoxin C1, C2 and C3 were designed. These primers were assigned into 3 pairs, SEQ. ID. NO. 1, SEQ. ID NO. 2 and SEQ. ID NO. 3, having specificity genes of enterotoxin C1, C2 and C3, respectively.

J. Synthesis of Oligonucleotide Primers

Those 4 PCR primers were synthesized with a DNA Synthesizer by Biotechnology Scientific Co., Taipei, Taiwan.

K. Polymerase Chain Reaction

To a 0.65-ml micro-centrifuge, 1 μl each of 10 mM dATP, 10 mM dCTP, mM dGTP, and 10 mM dTTP, 5 μl of 10×PCR buffer, 1 μl each of primers (50 pmol/μl), suitable amount of target DNA, suitable amount of 1 unit ProZyme, and sterile distilled water to a total amount of 50 μl. Finally, the mixture was covered with mineral oil. Reaction conditions used in each set of PCR was listed in Table 5.

L. Test of PCR Specificity and Sensitivity of Primers (1) Specificity:

To a 0.5-ml micro-centrifuge was added a formulated PCR reaction solution with a composition of: 200 μM dNTP (N=A-T-G-C), 1×PCR buffer, 25 or 50 pmole primers, a suitable amount of DNA, 0.4 unit Prozyme, and sterile distilled water to a total volume of 50 μl, and the mixture thus prepared was covered with one drop of mineral oil. Thereafter, the micro-centrifuge was placed in a PCR thermocycler and a three-step PCR was carried out under following conditions: 20 seconds at 94° C. to denaturing DNA into single strand; 35 cycles of lowering the temperature to the annealing temperature for each set of primers (Table 5), keeping at this temperature for 20 seconds for annealing the primers and raising the temperature to 72° C. for 30 seconds for polymerase extension; and finally, keeping at 72° C. for 5 minutes. All steps were controlled by the computer program and 10 μl aliquots of PCR products were taken for analysis as described below. Each sample was analyzed by electrophoresis on 2.0% agarose in 1×TAE buffer, stained with ethidium bromide, observed under a UV box and photographed.

(2) Sensitivity:

The bacteria suspension was serially diluted at 10×. DNA extraction was carried out with phenol/chloroform as described above. DNA thus obtained was dissolved in 10 μl sterile distilled water and the resulting solution was added in a previously prepared 40 μl PCR solution (200 μM dNTP, N=A, T, G, C). Thereafter, the solution was covered with one drop of mineral oil and PCR was performed as described above.

The invention will be described more detailed by means of the following non-limiting examples.

EXAMPLE 1

Results of the detection and sensitivity test performed on *S. aureus* stains producing standard staphylococcal enterotoxin C1, C2 and C3 and non-C type strains were listed in Table 1 and 2 as well as shown in FIGS. 1 and 2, wherein the PCR conditions were the same as described above. It is found that primers designed according to the invention produced specific PCR products only in their targeted enterotoxin-producing strains. These specific PCR products exhibited a size in consistent with the product size as predicted by the original design, i.e., 402 bp, 501 bp, and 672 bp, respectively. Among them, PCR using the primer set of ENTC1/ENTCR could detect standard enterotoxin-producing strain of type C, CCRC 12654 and FRI 137. The standard enterotoxin-producing strain of type C, CCRC 12654, was derived from strain ATCC 19095 that was isolated in the Food Research Institute of the Wisconsin University, USA, and assigned as FRI 137. Other non-staphylococcal bacterial strains could not produce PCR product. These results suggested that those three sets of primers, ENTC1/ENTCR, ENTC2/ENTCR, and ENTC3/ENTCR, exhibited extremely high degree of specificity with respect to genes of enterotoxin-producing *S. aureus* strains of subtypes C1, C2 and C3. Therefore, they can be used to detect whether genes of enterotoxin C1, C2 and C3 is present in a *S. aureus* strains strain. The result of sensitivity test revealed that, since PCR product could be produced using primer set ENTC1/ENTCR, ENTC2/ENTCR and ENTC3/ENTCR at a concentration of $10^0$, the sensitivity could be as high as $10^0$ CFU/ml.

EXAMPLE 2

PCR detections with primer sets ENTC1/ENTCR-ENTC2/ENTCR-ENTC3/ENTCR designed according to the invention were carried out on 39 enterotoxin-producing *S. aureus* strains type C that had been isolated in 20 cases of food poisoning by the Third Branch of the Disease Control Agency, the Health Administration, Executive Yuan, ROC during 1995-2000. PCR and analytical conditions were same as described above. The result is shown in Table 3.

It can be seen from Table 3 that identification of subtype C1, C2 and C3 performed on the above-mentioned 39 enterotoxin-producing *S. aureus* type C by PCR using primer sets according to the invention revealed one staphylococcal enterotoxin subtype C1, 12 strains of subtype C2, and 13 strains of subtype C3, as well as 13 strains of other type C. Therefore, among those pathogenic *S. aureus*, staphylococcal enterotoxin subtypes C2 and C3 are the prominent ones with a proportion of about 64%, and only 1 subtype C1 strain, while with about 33% of other subtype Cs.

EXAMPLE 3

PCR detections with primer sets ENTC1/ENTCR-ENTC2/ENTCR-ENTC3/ENTCR designed according to the invention were carried out on 10 enterotoxin-producing *S. aureus* strains type C (FRI strains No 202, 248, 293b, 406, 412, 414, 418, 423, 429, 623) that had been provided by the Food Research Institute (FRI) of the University of Wisconsin, Madison, Wis., USA. PCR and analytical conditions were same as described above. The result is shown in Table 3.

It can be seen from Table 3 that identification of subtype C1, C2 and C3 performed on the above-mentioned 39 enterotoxin-producing *S. aureus* type C by PCR using primer sets according to the invention revealed 8 staphylococcal enterotoxin strains of subtype C2, 1 strains of subtype C3, and 1 strains of other type C, while no subtype C1. Therefore, this result is similar to that of Example 2, i.e., among those pathogenic *S. aureus* type C, staphylococcal enterotoxin subtypes C2 and C3 are the prominent ones.

Many changes and modifications in the above-described embodiments of the invention can, or course, be carried out without departing from the scope thereof. Accordingly, to promote the progress in science and the useful arts, the invention is intended to be limited only by the scope of the appended claims.

TABLE 1

Specificity of the PCR primers for SEC1, SEC2, SEC3 and SEB genes of *Staphylococcus aureus* strains

| Source and Strain # | Enterotoxin type[a] | RPLA | PCR | PCR for SEC subtype | | |
|---|---|---|---|---|---|---|
| | | | | ENTC1/ ENTCR | ENTC2/ ENTCR | ENTC3/ ENTCR |
| CCRC 12657 | A | A | A | − | − | − |
| CCRC 12653 | B | B | B | − | − | − |
| CCRC 12654 | C | C | C | + | − | − |
| FRI 137 | C1 | C | C | + | − | − |
| FRI 361 | C2 | C | C | − | + | − |
| FRI 913 | C3 | C | C | − | − | + |
| CCRC 12660 | D | D | D | − | − | − |
| CCRC 12656 | E | ND[b] | E | − | − | − |
| CCRC 13831 | TSST-1 | TSST | TSST-1 | − | − | − |
| FRI 572 | G | ND | ND | − | − | − |
| FRI 569 | H | ND | ND | − | − | − |
| FRI 445 | I | ND | ND | − | − | − |

[a] Enterotoxin types are according to the information from strain source.
[b] ND: Not determined.

TABLE 2

PCR assay for bacteria strains other than SEC *S. aureus* using ENTC1/ENTCR, ENTC2/ENTCR and ENTC3/ENTCR primer pairs.

| Species | Source and strain # | PCR for SEC subtype | | |
|---|---|---|---|---|
| | | ENTC1/ ENTCR | ENTC2/ ENTCR | ENTC3/ ENTCR |
| *Staphylococcus aureus* | | | | |
| *S. aureus* SEC1 | FRI 137 | + | − | − |
| *S. aureus* SEC2 | FRI 361 | − | + | − |
| *S. aureus* SEC3 | FRI 913 | − | − | + |
| *S. aureus* (non-enterotoxigenic) | CCRC 011 | − | − | − |
| | CCRC 029 | − | − | − |
| | CCRC 033 | − | − | − |
| Other bacteria strains | | | | |
| *Staphylococcus epidermids* | CCRC 11030 | − | − | − |
| *Staphylococcus xylosus* | CCRC 12930 | − | − | − |
| *Streptococcus mutans* | CCRC 10793 | − | − | − |
| *Alcaligenes faecalis* | CCRC 10828 | − | − | − |
| *Bacillus cereus* | CCRC 10603 | − | − | − |
| *Bacillus psychrophilus* | CCRC 11738 | − | − | − |
| *Bacillus subtilis* | CCRC 10258 | − | − | − |
| *Bacillus thuringiensis* | CCRC 14683 | − | − | − |
| *Brevibacterium linens* | CCRC 10041 | − | − | − |
| *Clostridium perfringens* | CCRC 10914 | − | − | − |
| *Enterobacter aerogenes* | CCRC 10370 | − | − | − |
| *Erwinia carotovora* | CCRC 11298 | − | − | − |
| *Escherichia coli* | ATCC 35401 | − | − | − |
| *Hafnia alyei* | CCRC 10906 | − | − | − |
| *Klebsiella marcescens* | CCRC 10629 | − | − | − |
| *Kluyvera ascorbata* | CCRC 11645 | − | − | − |
| *Micrococcus roseus* | CCRC 11577 | − | − | − |
| *Micrococcus varians* | CCRC 11272 | − | − | − |
| *Morganella morganii* | CCRC 10706 | − | − | − |
| *Proteus vulgaris* | CCRC 10728 | − | − | − |
| *Salmonella enteritdis* | ATCC 13076 | − | − | − |
| *Salmonella typhimurium* | ATCC 14028 | − | − | − |
| *Serratia marcescens* | CCRC 13880 | − | − | − |
| *Proteus vulgaris* | CCRC 10728 | − | − | − |
| *Yersinia entreocolitica* | CCRC 10807 | − | − | − |

TABLE 3

PCR identification of the SEC1, C2 and C3 subtypes for SEC S. aureus strains obtained from randomly selected diarrhea patients engaged with food-borne outbreaks that occurred in central Taiwan between 1995 and 2000.

| Outbreaks no | Ratio of[a] diseased person | Date | Location | SEC strains identified[b] by SET-RPLA | Food Samples associated | $C_1$ | $C_2$ | $C_3$ | Other C |
|---|---|---|---|---|---|---|---|---|---|
| 1 | 121/402 | March 1995 | Yunlin | 1 | School lunch | | | 1 | |
| 2 | 12/51 | March 1995 | Nantou | 4 | Meal boxes | | 4 | | |
| 3 | 66/405 | March 1995 | Taichung | 2 | Meal boxes | | 2 | | |
| 4 | 21/38 | October 1995 | Miaoli | 1 | Meal boxes | | | 1 | |
| 5 | 22/201 | January 1996 | Taichung | 1 | Meal boxes | | | 1 | |
| 6 | 34/393 | January 1996 | Taichung | 2 | Meal boxes | | | 2 | |
| 7 | 15/1935 | March 1996 | Nantou | 1 | School lunch | | | 1 | |
| 8 | 20/120 | April 1996 | Taichung | 1 | Banquet | | | 1 | |
| 9 | 20/279 | January 1997 | Taichung | 1 | Meal boxes | | | 1 | |
| 10 | 44/862 | March 1997 | Taichung | 3 | Meal boxes | | 1 | 1 | 1 |
| 11 | 1036/1938 | March 1997 | Taichung | 9 | Meal boxes | 1 | 3 | 3 | 2 |
| 12 | 6/25 | October 1997 | Taichung | 3 | Meal boxes | | 1 | | 2 |
| 13 | 23/300 | December 1997 | Miaoli | 1 | Banquet | | | 1 | |
| 14 | 3/3 | December 1997 | Taichung | 1 | Lunch | | 1 | | |
| 15 | 78/350 | September 1998 | Nantou | 1 | Banquet | | | | 1 |
| 16 | 174/1070 | October 1998 | Taichung | 1 | Lunch | | | | 1 |
| 17 | 17/299 | November 1998 | Nantou | 2 | Lunch | | | | 2 |
| 18 | 121/840 | December 1998 | Miaoli | 2 | Other | | | | 2 |
| 19 | 17/571 | November 1998 | Changhua | 1 | Meal boxes | | | | 1 |
| 20 | 17/500 | June 1999 | Miaoli | 1 | Lunch | | | | 1 |
| Total number of strains identified | | | | 39 | | 1 | 12 | 13 | 13 |
| Total no. of outbreaks associated with each SEC subtype | | | | | | 1 | 6 | 10 | 9 |

[a] The number of diseased persons over the number of total attendants.
[b] Fecal samples from selected diseased persons were collected and subjected to SET-RPLA assay bythe Third Branch of National Center for Disease Control, Taichung, Taiwan. Randomly selected SECstrains were used in this study.
[c] SEC subtypes were determined by PCR. SEC strains not grouped in SEC1, C2 and C3 subtypes were termed as other SEC subtype.

TABLE 4

PCR detection of the SEC subtypes for randomly selected SEC strains obtained from FRI[a].

| | | | PCR for C type | | |
|---|---|---|---|---|---|
| Lab. no. | strain Source | Enterotoxin type | ENTC1/ ENTCR | ENTC2/ ENTCR | ENTC3/ ENTCR |
| 6013 | FRI-202 | C | − | + | − |
| 6069 | FRI-248 | C | − | + | − |
| 6070 | FRI-293[b] | C | − | − | − |
| 6071 | FRI-406 | C | − | + | − |
| 6072 | FRI-412 | C | − | + | − |
| 6073 | FRI-414 | C | − | + | − |
| 6074 | FRI-418 | C | − | + | − |
| 6075 | FRI-423 | C | − | + | − |
| 6076 | FRI-429 | C | − | − | + |
| 6077 | FRI-623 | C | − | + | − |
| Total | | 10 | 0 | 8 | 1 |

[a] FRI: Food Research Institute, Univ. of Wisconsin, Madison, WI, USA.
[b] Strain of FRI-293 may belong to SEC subtypes other than SEC1, C2 and C3.

TABLE 5

The PCR conditions used in this study

| Target gene | Primers | PCR condition[a] | Size of PCR product (bp) |
|---|---|---|---|
| entC1 | ENTC1/ENTCR | 94° C./30 sec<br>55° C./30 sec<br>72° C./20 sec | 402 |
| entC2 | ENTC2/ENTCR | 94° C./30 sec<br>59° C./20 sec<br>72° C./20 sec | 501 |
| entC3 | ENTC3/ENTCR | 94° C./30 sec<br>59° C./20 sec<br>72° C./20 sec | 672 |

[a] Total cycles are 35, the first denature time is 3 min at 94° C., and the final extension time is 3 min at 72° C.

REFERENCES

1. "Food poisoning status in Taiwan area in 1998", the Administration Department, Executive Yuan, Taipei, Taiwan.
2. Altboum, Z., I. Hertman, and S. Sarid. 1985. Penicillinase plasmidlinked genetic determinants for enterotoxin B and C1 production in Staphylococcus aurezis. Infect. Immun. 47: 514-521.
3. Becker, K., R. Roth, and G. Peter. 1998. Rapid and specific detection of toxigenic Staphylococcus aureus: use two multiplex PCR enzyme immunoassays for amplification and hybridization of staphylococcal enterotoxin genes, exfoliative toxin gene, and toxic shock syndrome toxin 1 gene. J. Clin. Microbiol. 36: 2548-2533.
4. Beikum, A., R. Bax, P. Peerbooms, W. H. R Goessens, N. Ceeuwen, and W. G. V. Quint. 1993. Comparison of phage typing and DNA fingerprinting by polymerase chain reaction for discrimination of methicillin-resistant *Staphylococcus aureus* strains. J. Clin. Microbiol. 31: 798-803.
5. Bennett, R. W., and G. A. Lancette. 1992. *Staphylococcus aureus*, pp. 161-166. In Bacteriological Analytical Manual, 7th ed. Association Official Analytical Chemists International, Arlington, Va.
6. Bergdoll, M. S., C. R. Borja, and R. M. *Avena*. 1965. Identification of a new enterotoxin as enterotoxin C. J. Bacteriol. 90: 1481-1485.
7. Bergdoll, M. S., C. R. Borja, R. N. Robbins, and K. F. Weiss. 1971. Identification of staphylococcal enterotoxin E. Infect. Immun. 4: 593595.
8. Bergdoll, M. S., M. J. Surgalla, and G. M. Dack. 1959. Identification of staphylococcal enterotoxin B. J. Immunol. 83: 334-338.
9. Betley, M. J., and T. O. Harris. 1994. Staphylococcal enterotoxin: genetic characterization and relationship between structure and emetic activity. J. Food Microbiol. 11: 109-121.
10. Betley, M. J., and Harris, T. O. 1994. Staphylococcal enterotoxin: genetic characterization and relationship between structure and emetic activity. Food Microbiol. 11:109-121.
11. Bohach, G. A., and P. M. Schlievert. 1987. Nucleotide sequence of the staphylococcal enterotoxin C1 gene and relatedness to other pyrogenic toxins. Mol. Gen. Genet. 209: 15-20.
12. Bohach, G. A., and P. M. Schlievert. 1989. Conservation of the biologically active portions of staphylococcal enterotoxin C1 and C2. Infect. Immun. 57: 2249-2252.
13. Bohach, G. A., B. N. Kreiswirth, R. P. Novick, and P. M. Schlievert. 1989. Analysis of toxic shock syndrome isolates producing staphylococcal enterotoxin B and C1 with use of southern hybridization and immunologic assays. Rev. Infect. Dis. I 1: S75-S82.
14. Bohach, G. A., J. P. Handley, and P. M. Schlievert. 1989. Biological and immunological properties of the carboxyl terminus of staphylococcal enterotoxin C1. Infect. Immun. 57:23-28.
15. Bohach, G. A., and Schlievert, P. M. 1987. Nucleotide sequence of the Staphylococcal enterotoxin C1 gene and relatedness to other pyrogenic toxins. Mol. Gen. Genet. 209:15-20.
16. Borja, C. R., and M. S. Bergdoll. 1967. Purification and partial characterization of enterotoxin C produced by *Staphylococcus aureus* strain 137. Biochem. 6: 1467-1473.
17. Brehm, R. D., H. S. tranter, P. Hambleton, and J. Melling. 1990. Large-scale purification of staphylococcal enterotoxin A, B, and C2 by dye ligand affinity chromatography. Appl. Environ. Microbiol. 56: 1067-1072.
18. Couch, J. L., and M. J. Betley. 1989. Nucleotide sequence of the type C3 staphylococcal enterotoxin gene suggests that intergenic recombination causes antigenic variation. J. Bacteriol. 171: 4507-4510.
19. Couch, J. L., and Betley, M. J. 1989. Nucleotide sequence of the type C3 Staphylococcal enterotoxin gene suggests that intergenic recombination causes antigenic variation. J. Bacteriol. 171:4507-4510.
20. Freed, R. C., M. L. Evenson, R. F. Reiser, and M. S. Bergdoll. 1982. Enzyme-linked immunosorbent assay for detection of staphylococcal enterotoxin in foods. Appl. Environ. Microbiol. 44: 1349-1355.
21. Hovde, C. J., J. C. Marr, M. L. Hoffmann, K. Crum, Dennis, D. L. Stevens, C. V. Stauffacher, and G. A. Bohach. 1994. Investigation of the role of the disulphide bond in the activity and structure of staphylococcal enterotoxin C I. Mol. Microbiol. 13: 897-909.
22. Hovde, C. J., S. P. Hackett, and G. A. Bohach. 1990. Nucleotide sequence of the staphylococcal enterotoxin C3 gene: sequence comparison of all three type C staphylococcal enterotoxin. Mol. Gen. Genet. 220: 329-333.
23. Huang, 1. Y., T. Shih, C. R. Borja, R. M. Avena, and M. S. Bergdoll. 1967. Amino acid composition and terminal amino acids of staphylococcal enterotoxin C. Biochem. 6: 1480-1483. J. Med. 316: 927-93 1.
24. Johnson, W. M., S. D. T'yler, E. D. Ewan, F. E. Ashton, D. R. Pollard, and K. R. Rozee. 1991. Detection of genes for enterotoxin, exfoliative toxin, and toxic shock syndrome toxin I in *Staphylococcus aureus* by the polymerase chain reaction. J. Clin. Microbiol. 29: 426430.
25. Kawabata, A., S. Ichiyama, Y. Iinuma, Y. Hasegawa, M. Ohta, and K. Shimokata. 1997. Exfoliative toxin detection using reversed passive latex agglutination: clinical and epiderrniologic applications. J. Clin. Microbiol. 35: 1984-1987.
26. Kokan, N. P., and M. S. Bergdoll. 1987. Detecting of low-enterotoxin producing *Staphylococcus aureus* strains. Appl. Environ. Microbiol. 53: 2675-2676.
27. Kumari, D. N. P., V. Keer, P. M. Hawkey, P. Parnell, N. Joseph, J. R Richardson, and B. Cookson. 1997. Comparison and application of ribosome spacer DNA amplicon polymorphisms and pulsed-field gel electrophoresis for differentiation of methicillin-resistant *Staphylococcus aureus* strains. J. Clin. Microbiol. 35: 881-885.
28. Maes, N., Y. D. Gheldre, R. D. Ryck, M. Vaneechoutte, H. Meugnier, J. Etienne, and M. J. Struelens. 1997. Rapid and accurate identification of *Staphylococcus* species by TRNA intergenic spacer length polymorphism analysis. J. Clin. Microbiol. 35: 2477-2481.
29. Marr, J, C., J. D. Lyon, J. R. Roberson, M. Lupher, W. C. Davis, and G. A. Bohach. 1993. Characterization of novel type C staphylococcal enterotoxin: biological and evolutionary implications. Infect. Immun. 61: 4254-4262.
30. Metzger, J. F., A. D. Johnson, and L. Spero. 1975. Intrinsic and chemically produced microheterogeneity of Stapylococcus aureus enterotoxin type C. Infect. Immun. 12: 93-97.
31. Meyer, R. E, and M. J. Palmieri. 1980. Single radial immunodiff-usion method for screening staphylococcal isolates for enterotoxin. Appl. Environ. Microbiol. 40: 1080-1085.
32. Miller, B. A., R. F. Reiser, and M. S. Bergdoll. 1978. Detection of staphylococcal enterotoxin A, B, C, D, and E in foods by radioimmunoassay, using staphylococcal cells containing protein A as immunoadsorbent. Appl. Environ. Microbiol. 3 6: 421-426.
33. Murakami, K., W. Minamide, K. Wada, E. Nakamura, H. Teraoka, and S. Watanabe. 1991. Identification of methicillin-resistant strains of staphylococci by polymerase chain reaction. J. Clin. Microbiol. 29: 2240-2244.
34. Murono, K., K. Fujita, and H. Yoshioka. 1988. Detection of staphylococcal exfoliative toxin by slide latex agglutination. J. Clin. Microbiol. 26: 271-274.
35. Neill, R. J., G. R. Fanning, F. Delahoz, R. Wolff, and P. Gemski. 1990. Oligonucleotide probes for detection and differentiation of *Staphylococcus aureus* strains containing genes for enterotoxin A, B, and C and toxic hock syndrome toxin 1. J. Clin. Microbiol. 28: 15141548.
36. Otero, A., M. L. Garcia, M. C. Farcia, B. Moreno, and M. S. Bergdoll. 1990. Production of staphylococcal enterotoxin C1 and C2 and thertnonuclease throughout the growth cycle. Appl. Environ. Microbiol. 56: 555-559

37. Park, C. E., and R. Szabo. 1986. Evaluation of the reversed passive latex agglutination (RPLA) test kits for detection of staphylococcal enterotoxin A B, C, and D in foods. Can. J. Microbiol. 32: 723-727.
38. Piemont, Y, M. Haubensack, and H. Monteil. 1984. Enzyme-linked immunosorbent assays for *Staphylococcus aureus* exfoliative toxins A and B and some applications. J. Clin. Microbiol. 20: 1114-112 1.
39. Prevost, G., B. Pottecher, M. Dahlet, M. Bientz, J. M. Mantz, and Y. Piemont. 1991. Pulsed field gel electrophoresis as a new epidemiological tool for monitoring methicillin-resistant *Staphylococcus aureus* in an intensive care unit. J. Hosp. Infect. 17: 225-269.
40. Rasooly, L., N. R. Rose, D. B. Shah, and A. Rasooly. 1997. In vitro assay of *Staphylococcus aureus* enterotoxin A activity in food. Appl. Environ. Microbiol. 63: 2361-23265.
41. Regassa, L. B., and M. J. Betley. 1993. High sodium chloride concentrations inhibit stapylococcal enterotoxin C gene (sec) expression at the level of sec m RNA. Infect. Immun. 61: 1581-1585.
42. Regassa, L. B., J. L. Couch, and M. J. Betley. 1991. Steady-state staphylococcal enterotoxin type C MRNA is affected by a product of the accessory gene regulator (agr) and by glucose. Infect. Immun. 59: 955-962.
43. Reiser, R. F., R. N. Robbins, A. Noleto, G. P. Khoe, and M. S. Bergdoll. 1984. Identification, purification, and some physicochemical properties of staphylococcal enterotoxin C3. Infect. Immun. 45: 625-630.
44. Rifai, S., V. Barbancon, G. Prevost, and Y. Piemont. 1989. Synthetic exfoliative toxin A and B DNA probes for detection of toxigenic *Staphylococcus aureus* strains. J. Clin. Microbiol. 27: 504-506.
45. Robbins, R., S. Gould., and M. S. Bergdoll. 1974. Detecting the enterotoxigenicity of *Staphylococcus aureus* strains. Appl. Microbiol. 28: 946-950.
46. Roberson, J. R., L. K. Fox, D. D. Hancock, and T. E. Besser. 1992. Evaluation of methods for differentiation of coagulase-positive staphylococci. J. Clin. Microbiol. 30: 3217-3219.
47. Sakurai, S., H. Suzuki, and K. Machida. 1995. Rapid identification by polymerase chain reaction of staphylococcal exfoliative toxin serotype A and B genes. Microbiol. Immunol. 39: 379-386.
48. S-autuier, P., C. Bourneix, G. Prevost, -and A. Xudermont. 1993. Random amplified polymorphic DNA assay is less discriminant than pulsed field gel electrophoresis for typing strains of methicillin-resistant *Staphylococcus aureus*. J. Clin. Microbiol. 31: 982-985.
49. Schmidt, J. J., and L. Spero. 1983. The complete amino acid sequence of staphylococcal enterotoxin C I. J. Biol. Chem. 258: 6300-6306.
50. Schmitz, F. J., Steiert, M., Hofmann, B., Verhoef, J., Hadding, U., Heinz, H. P., and Kohrer, K. 1998. Development of a multiplex-PCR for direct detection of the genes for enterotoxin B and C, and toxic shock syndrome toxin-1 in *Staphylococcus* arueus isolates. J. Med. Microbiol. 47:335-340.
51. Thompson, N. E., M. Razdan, G. Kuntsmann, J. M. Aschenbach, M. L. Evenson, and M. S. bergdoll. 1986. Detection of staphylococcal enterotoxin by enzyme-linked immunosorbent assays and radioimmunoassays: comparison of monoclonal and polyclonal antibody systems. Appl. Environ. Microbiol. 51: 885-890.
52. Tsen, H. Y., T. R. Chen, and G. Y. Yu. 1994. Detection of B and C types enterotoxigenic *Staphylococcus aureus* using polymerase chain reaction. J. Chinese Argic. Chem. Sci. 32: 322-331.
53. Tsen, H. Y., and Chen, T. R. 1992. Use of the polymerase chain reaction for specific detection of type A, D and E enterotoxigenic *Staphylococcus aureus* in foods. Appl. Microbiol. Biotech. 37:685-690.
54. Tsen, H. Y., Chen, T. R. and Yu, G. K. 1994. Detection of B, C types enterotoxigenic *Staphylococcus aureus* using polymerase chain reaction. J. Chinese Agric. Chem. Soci. 32:322-331.
55. Tsen, H. Y, R. Y Yang, and F. Y Huang. 1993. Novel oligonucleotide probes for identification of enterotoxigenic *Staphylococcus aureus*. J. Ferrn. Bioeng. 76: 7-13.
56. Unal, S., J. Hoskins, J. E. Flokowitsch, C. Y. E. Wu, D. A. Preston, and P. L. Skatrud. 1992. Detection of methicillin-resistant staphylococcal by using the polymerase chain reaction. J. Clin. Microbiol. 30: 1685-1691.
57. Whiting, J. Log Po M. Rosten, and A. W. Chow. 1989. Determination by western blot (immunoblot) of seroconversions to toxic shock syndrome (TSS) toxin I and enterotoxin A, B, or C during Infection with TSS- and non-TSS-associated *Staphylococcus aureus*. Infect. Immun. 57:231-234.
58. Wieneke, A. A. 1991. Comparison of four kits for the detection of staphylococcal enterotoxin in foods from outbreaks of food poisoning. Int. J. Food Microbiol. 14: 305-312.
59. Wilson, 1. G., J. E. Cooper, and A. Gilmour. 1994. Some factors inhibiting amplification of the *Staphylococcus aureus* enterotoxin C, gene (sec') by PCR. Int. J. Food Microbiol. 22: 55-62.
60. Wilson, 1. G.9 J. E. Cooper, and A. Gilmour. 1991. Detection of enterotoxigenic *Staphylococcus aureus* in dried Skimmed milk: use of the polymerase chain reaction for amplification and detection of staphylococcal enterotoxin genes entb and entcl and the thermonuclease gene nuc. Appl. Environ. Microbiol. 57: 1793-1798.
61. Wuepper, K. D., D. H. Baker, and R. L. Dimond. 1976. Measurement of the staphylococcal epidermolytic toxin: a comparison of bioassay, radial immunodiffusion, and radioimmunoassay. J. Invest. Dermatol. 67: 526-531.

What is claimed is:

1. A primer useful in polymerase chain reaction for the identification of subtypes $C_1$, $C_2$ and $C_3$ of staphylococcal enterotoxin type C, useful as primer in rapid PCR detection of enterotoxin-producing *Staphylococcus aureus* strain of subtype $C_1$, $C_2$ and $C_3$ present in food and clinical samples, comprising one of the following sequences:

SEQUENCE ID NO. 1 ACAGA GTTAT TAAAT GAAGG ATCAT ACCAA AAAGT ATTGC

SEQUENCE ID NO. 2 GTATC AGCAA CTAAA GTTAT ATCAT ACCAA AAAGT ATTGC

SEQUENCE ID NO. 3 AAGAG ATTAT TTATT TCACGT ATCAT ACCAA AAAGT ATTGC.

2. A DNA probe, useful in PCR reaction for the identification of subtypes $C_1$, $C_2$ and $C_3$ in staphylococcal enterotoxin type C, comprising one of the following sequences:

SEQUENCE ID NO. 1 ACAGA GTTAT TAAAT GAAGG ATCAT ACCAA AAAGT ATTGC

SEQUENCE ID NO. 2 GTATC AGCAA CTAAA GTTAT ATCAT ACCAA AAAGT ATTGC

SEQUENCE ID NO. 3 AAGAG ATTAT TTATT TCACGT ATCAT ACCAA AAAGT ATTGC.

* * * * *

SEQUENCE LISTING

<160> NUMBER OF SEQ ID NOS: 3

<210> SEQ ID NO 1
<211> LENGTH: 40
<212> TYPE: DNA
<213> ORGANISM: Staphylococcus aureus -continued

```
<400> SEQUENCE: 1
acagagttat taaatgaagg atcataccaa aaagtattgc                          40

<210> SEQ ID NO 2
<211> LENGTH: 40
<212> TYPE: DNA
<213> ORGANISM: Staphylococcus aureus

<400> SEQUENCE: 2
gtatcagcaa ctaaagttat atcataccaa aaagtattgc                          40

<210> SEQ ID NO 3
<211> LENGTH: 40
<212> TYPE: DNA
<213> ORGANISM: Staphylococcus aureus

<400> SEQUENCE: 3
aagagattat ttatttcacg atcataccaa aaagtattgc                          40
```